United States Patent
Leleti et al.

(10) Patent No.: US 11,401,273 B2
(45) Date of Patent: Aug. 2, 2022

(54) ASYMMETRIC SYNTHESIS OF AZASPIRO COMPOUNDS

(71) Applicant: PIRAMAL PHARMA LIMITED, Mumbai (IN)

(72) Inventors: Rajender Reddy Leleti, Gujarat (IN); Yogesh Waman, Gujarat (IN); Priya Kallure, Gujarat (IN); Zubeda Begum, Gujarat (IN); Thumban Divya, Gujarat (IN); Kumara Swamy Nalivela, Gujarat (IN); Saurabh Vijay, Gujarat (IN); Paranjay Parikh, Gujarat (IN); Sharadsrikar Kotturi, Gujarat (IN); Chirag Patel, Gujarat (IN); Krishna Nayak, Gujarat (IN); Kasimraza Baharooni, Gujarat (IN); Vinkal Zalavadiya, Gujarat (IN)

(73) Assignee: PIRAMAL PHARMA LIMITED, Mumbai (IN)

( * ) Notice: Subject to any disclaimer, the term of this patent is extended or adjusted under 35 U.S.C. 154(b) by 0 days.

(21) Appl. No.: 17/290,846

(22) PCT Filed: Nov. 19, 2019

(86) PCT No.: PCT/IB2019/059919
§ 371 (c)(1),
(2) Date: May 3, 2021

(87) PCT Pub. No.: WO2020/104930
PCT Pub. Date: May 28, 2020

(65) Prior Publication Data
US 2022/0041609 A1    Feb. 10, 2022

(30) Foreign Application Priority Data
Nov. 20, 2018   (IN) .............................. 201821043748

(51) Int. Cl.
| C07D 487/10 | (2006.01) |
| C07D 205/12 | (2006.01) |
| C07D 409/04 | (2006.01) |
| C07D 333/20 | (2006.01) |
| C07C 313/06 | (2006.01) |

(52) U.S. Cl.
CPC .......... *C07D 487/10* (2013.01); *C07C 313/06* (2013.01); *C07D 205/12* (2013.01); *C07D 333/20* (2013.01); *C07D 409/04* (2013.01)

(58) Field of Classification Search
CPC ................ C07D 487/10; C07D 205/12; C07D 333/20; C07D 409/04; C07C 313/06
USPC ......................................................... 548/952
See application file for complete search history.

(56) References Cited

U.S. PATENT DOCUMENTS 5,698,548 A    12/1997   Dugar et al.

FOREIGN PATENT DOCUMENTS

WO    2017/059191 A1    4/2017

OTHER PUBLICATIONS

ISR for International Application PCT/IB2019/059919, 2020.
Written Opinion for International Application PCT/IB2019/059919, 2020.
Manas K. Ghorai, et al., "Stereoselective synthesis of activated 2-arylazetidines via imino-aldol reaction", Org. Biomol. Chem., (20150000), vol. 13, pp. 9042-9049, XP055710668 [A] . see p. 9044, Table 2 & 3, 2015.
Amit A.Kudale, et al., "Asymmetric synthesis of 2-substituted cyclic amines", Tet. Lett., (20140000), vol. 55, doi:10.1016/j.tetlet.2014.11.022, pp. 7219-7221, XP029102391 [A] Scheme 1, p. 7220, 2014.
Leleti Rajender Reddy, et al., "Asymmetric synthesis of 1-substituted 2-azaspiro[3.3]heptanes: important motifs for modern drug discovery", Chem. Commun., (20190000), vol. 55, pp. 5068-5070, XP055710667 [PX] 1-9 whole document, 2019.
Leleti Rajender Reddy, et al., "Asymmetric Synthesis 1-Substituted 2,6-Diazaspiro[3.3], 2019 heptanes through Addition of 3-Azetidinecarboxylate Anions to Davis-Ellman Imines", Org. Lett., (20190000), vol. 21, pp. 3481-3484, XP055710664 [PX] 1-9 . whole document.

*Primary Examiner* — Kristin A Vajda
(74) *Attorney, Agent, or Firm* — Ladas & Parry LLP

(57) ABSTRACT

The present invention relates to an improved asymmetric synthesis of azaspiro or diazaspiro compound (hereafter referred to as the compound 5, ($5^A$) or ($5^N$)) or their pharmaceutically acceptable salts and derivatives; through the formation of intermediate compounds 4, ($4^A$) or ($4^N$) respectively. The process comprises an unusual substrate specific highly diastereoselective as well as enantio-enriched 1-substituted 2-azaspiro[3.3]heptane or 1-substituted 2-diazaspiro[3.3]heptane compounds with high diastereoselectivity by addition of a cyclobutane carboxylate anion to a Davis-Ellman's imine, followed by reduction and cyclisation resulting in the selective formation of azaspiro or diazaspiro intermediate compound 4, ($4^A$) or ($4^N$); which on subsequently removing the sulfinyl group provides corresponding azaspiro or diazaspiro compound 5, ($5^A$) or ($5^N$) respectively.

9 Claims, 1 Drawing Sheet

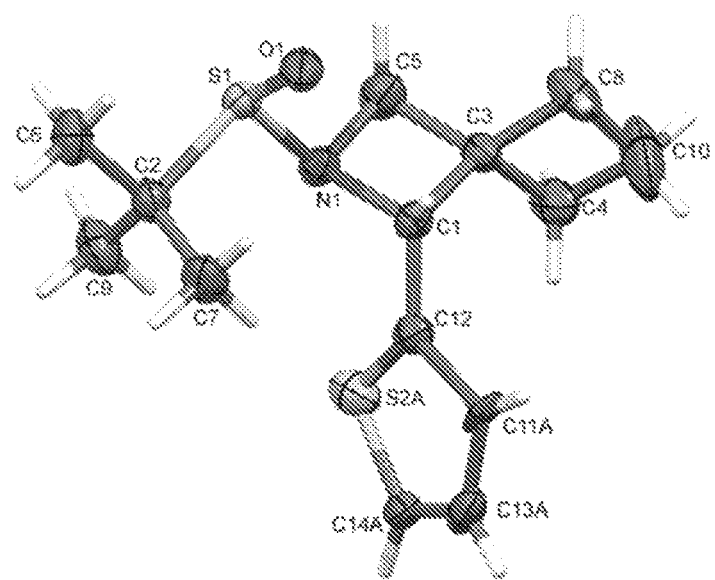

ASYMMETRIC SYNTHESIS OF AZASPIRO COMPOUNDS

This application is a national phase entry under 35 USC 371 of International Patent Application No.: PCT/IB2019/059919 filed on 19 Nov. 2019, which claims the benefit of Indian Application No. 201821043748 filed on 20 Nov. 2018, the entire content of which is incorporated by reference.

FIELD OF THE INVENTION

The present invention relates to an improved asymmetric synthesis of Azaspiro compound (hereafter referred to as the compound ($5^A$)) or their pharmaceutically acceptable salts and derivatives; through the formation of intermediate compounds ($4^A$).

BACKGROUND OF THE INVENTION

The following discussion of the prior art is intended to present the invention in an appropriate technical context, and allows its significance to be properly appreciated. Unless clearly indicated to the contrary, reference to any prior art in this specification should not be construed as an expressed or implied admission that such art is widely known or forms part of common general knowledge in the field.

The compounds of formula ($5^A$), 1-Substituted 2-Azaspiro compounds and relative 1-Substituted 2-Azaspiro[3.3]heptane compounds (5) are ubiquitous structural motifs present in many drugs, investigational drug candidates, bioactive substances as well as natural products. The azaspiro compounds of formula ($5^A$) and precisely azaspiro compound (5) and diazaspiro compound ($5^N$) are structurally represented as follows;

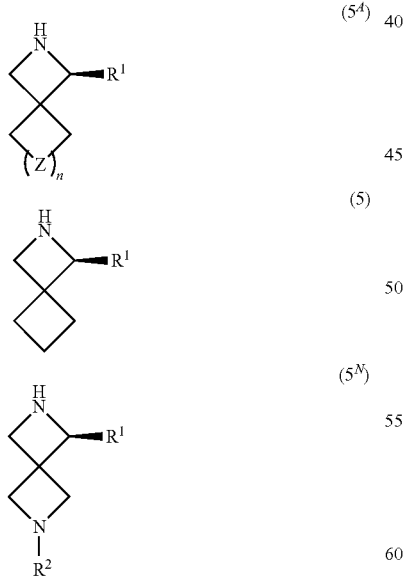

wherein, $R^1$ is independently selected from H, $C_1$-$C_{10}$ linear or branched or cyclic alkyl, substituted or unsubstituted aryl, ester, ether, hetero aryl, halo, haloalkyl; 'z' is selected from C, N, S or O; and n=0 to 7; $R^2$ is independently selected from H, alkyl, aryl or N-protecting group.

The azaspiro compounds of formula (5) being important intermediates for several bioactive compounds; a number of processes for its preparation are known in the art. The compound (5) can be used in synthesis of investigational drug candidates, such as PI3Ks inhibitor compounds, BTK inhibitor compounds and several antibacterial agents as represented below:

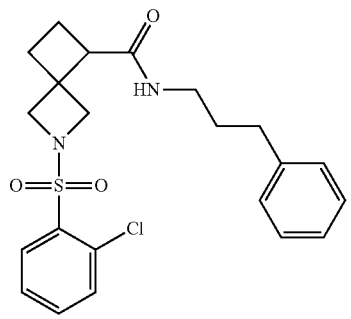

sEH inhibitor

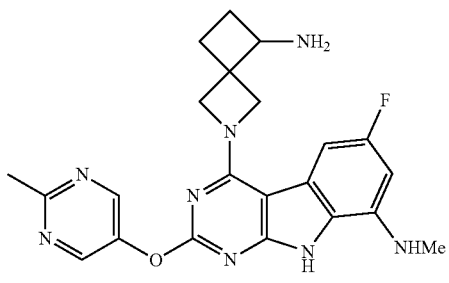

Antibacterial agent

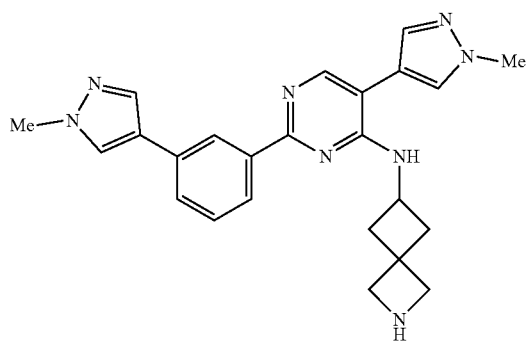

IRAKs inhibitor

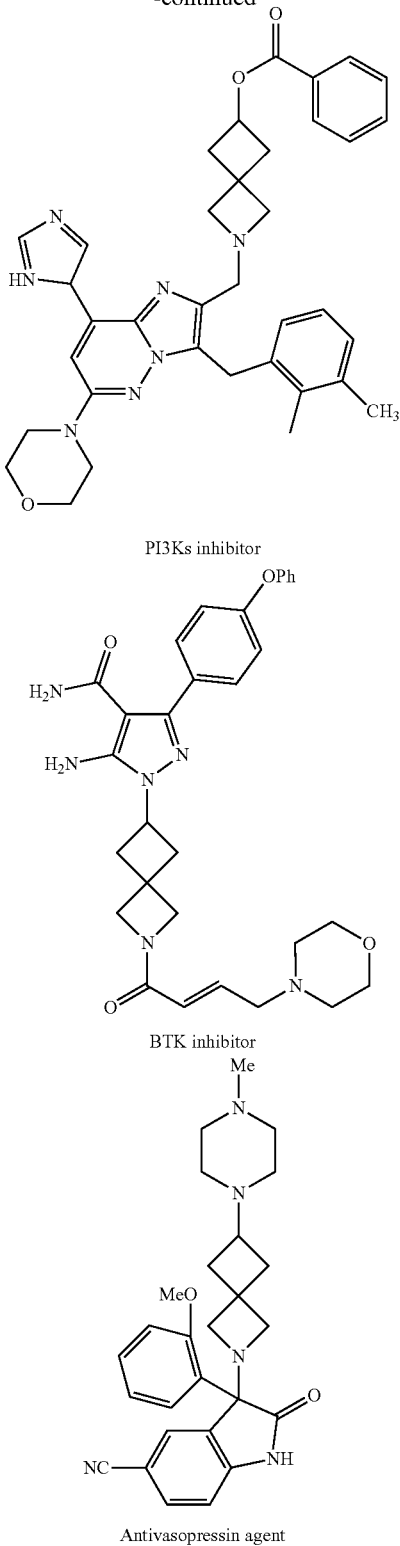

PI3Ks inhibitor

BTK inhibitor

Antivasopressin agent

The journal article Angewandte Chemie International Edition 56 (30), p. 8865-8869 (2017) demonstrated that the 1-substituted 2-azaspiro[3.3]heptanes result due to conformational restrictions of 2-substituted piperazines. These 1-substituted 2-azaspiro[3.3]heptanes are shown with better physicochemical properties compared to 2-substituted pip-eridines, such as the basicity (pKa), lipophilicity (log D), solubility ($Sol_{int}$), and clearance rates ($CL_{int}$). The article disclosed synthesis of azaspiro compound as depicted below, however the product obtained is racemic which may require further isomeric separation and also the product is obtained with poor yield.

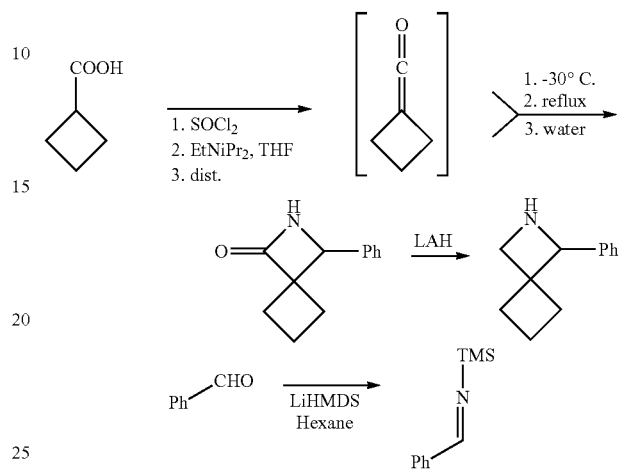

The U.S. Pat. No. 5,698,548 disclosed a process for azaspiro compound comprising converting the carboxylic acid compound to the corresponding acid chloride by refluxing with a reagent such as oxalyl chlorine in an inert solvent such as dichloromethane. The acid chloride is then refluxed with an imine in an inert solvent such as dichloromethane, heptane or toluene, in the presence of a trialkylamine such as triethylamine, tributylamine or diisopropylethylamine; as depicted below:

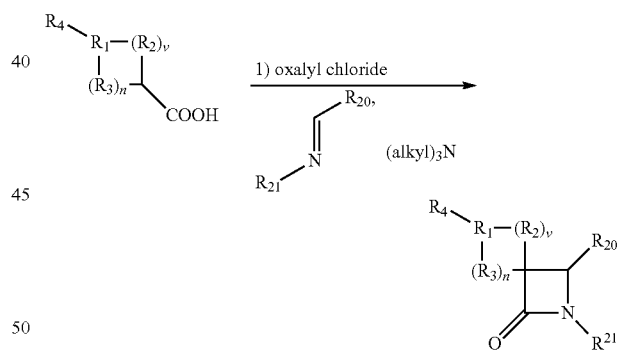

It is evident from the above cited references that the reported processes for the preparation of 1-Substituted 2-Azaspiro compounds ($5^A$) and relative 1-Substituted 2-Azaspiro[3.3]heptane compounds (5), primarily involve critical reaction conditions, reagents and lengthy workup procedures. For instance, the prior art procedure provides racemic compound, which subsequently requires further separate resolution procedure that affects the yield of the product and subsequently renders the process costlier. Also, the reported processes involves use of chlorination agents such as thionyl chloride and oxalyl chloride, which are hazardous at high scale manufacturing, hence the process is not industrially feasible.

In view of these drawbacks, there is a need to develop an industrially viable commercial process for the preparation of the compounds of formula ($5^A$) and compound (5); which is simple, efficient and cost-effective process and provides the desired compounds in improved yield and purity.

Inventors of the present invention had observed that the asymmetric synthesis for 1-substituted 2-azaspiro[3.3]heptane compounds remain unknown in the literature. The inventors of the instant invention reasoned that a direct method to access enantiopure 1-substituted 2-azaspiro[3.3] heptane compounds would be an asymmetric synthesis comprising addition of a cyclobutane carboxylate anion to a Davis-Ellman's imine, followed by reduction and cyclisation, which has not been explicitly reported in the art on the currently considered chemical moieties. Inventors of the present invention have developed an improved process that addresses the problems associated with the processes reported in the prior art, wherein the inventors report a straightforward, scalable and highly diastereoselective method that provides enantio-enriched 1-substituted 2-azaspiro[3.3]heptane compounds in high yields. The inventors envisage that this synthetic effort could be of value in a variety of research applications, including the discovery of the known as well as new bioactive substances, and also can be extended to broad substrate scope that includes various chemical entities and investigational drug candidates. The process of the present invention does not involve use of any toxic, critical and/or costly catalysts, solvents and reagents. Moreover, the process does not require additional purification, chiral separation or resolution and critical crystallization procedure. Accordingly, the present invention provides a process for the preparation of the 1-substituted 2-azaspiro[3.3]heptane compounds ($5^A$) as well as compound (5) and its intermediates; which is simple, efficient, cost effective, environmentally friendly and commercially scalable for large scale operations.

SUMMARY OF THE INVENTION

In one aspect, the present invention relates to an improved process for the preparation of azaspiro or diazaspiro compound ($5^A$) comprising, reacting ester compound ($1^A$) with N-tert-butanesulfinylimine (2) in presence of a base to produce ester intermediate ($3^A$); followed by reduction and cyclization of the compound ($3^A$) to form azaspiro intermediate compound ($4^A$); and subsequently removing the sulfinyl group.

In one aspect, the present invention relates to an improved process for the preparation of azaspiro compound (5) comprising, reacting ester compound (1) with N-tert-butanesulfinylimine (2) in presence of a base to produce ester intermediate (3); followed by reduction and cyclizing the compound (3) to form azaspiro intermediate compound (4); and subsequently removing the sulfinyl group.

In one aspect, the present invention relates to an improved process for the preparation of azaspiro intermediate compounds (4) comprising, reacting cyclobutane carboxylate ester compound (1') with N-tert-butanesulfinylimine (2) in presence of Lithium bis(trimethylsilyl)amide (LiHMDS) to produce cyclobutane carboxylate ester intermediate (3'); followed by reduction and cyclization of the compound (3').

In one aspect, the present invention relates to an improved process for the preparation of azaspiro compound ($5^A$) comprising, (a) reacting ester compound ($1^A$) with N-tert-butanesulfinylimine (2) in the presence of lithium base, (b) reduction and cyclization of the compound ($3^A$) of stage (a) to form azaspiro intermediate compound ($4^A$), (c) removing the sulfinyl group from the azaspiro intermediate compound ($4^A$) of stage (b).

In one aspect, the present invention relates to an improved process for the preparation of diazaspiro compound ($5^N$) comprising, reacting ester compound ($1^N$) with N-tert-butanesulfinylimine (2) in presence of a lithium base to produce ester intermediate ($3^N$); followed by reduction and cyclization of the compound ($3^N$) to form diazaspiro intermediate compound ($4^N$); and subsequently removing the sulfinyl group.

BRIEF DESCRIPTION OF THE DRAWINGS

FIG. 1) depicts X-ray crystal structure of compound (4l).

DETAILED DESCRIPTION OF THE INVENTION

Accordingly, the present invention relates to an improved process for the preparation of azaspiro or diazaspiro compound ($5^A$) represented by the following formula,

wherein, $R^1$ is independently selected from H, $C_1$-$C_{10}$ linear or branched or cyclic alkyl, substituted or unsubstituted aryl, ester, ether, hetero aryl, halo, haloalkyl; 'z' is to selected from C, N, S or O; and n=0 to 7.

comprising the steps of:
(a) reacting ester compound ($1^A$) represented by the following formula,

wherein, R is independently selected from H, $C_1$-$C_{10}$ linear or branched or cyclic alkyl, substituted or unsubstituted aryl, ester, ether, hetero aryl, halo, haloalkyl; 'z' is selected from C, N, S or O; and n=0 to 7.
with sulfinylimine compound (2') represented by the following formula,

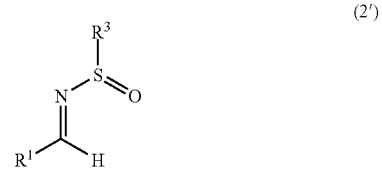

wherein, $R^3$ is independently selected from t-butyl or p-tolyl;
in the presence of base, to provide compound ($3^{A'}$);
(b) reducing and cyclization of the compound ($3^{A'}$) of stage (a) represented by the following formula,

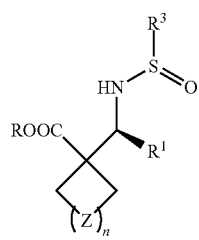

(3^{A'})

in the presence of a reducing agent, to provide compound (4^{A'});

(c) removing the sulfinyl group from the azaspiro intermediate compound (4^A) of stage (b) represented by the following formula,

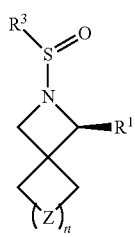

(4^{A'})

to provide compound (5^A).

Also accordingly, the present invention relates to an improved process for the preparation of azaspiro compound (5^A) represented by the following formula,

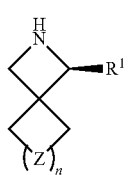

(5^A)

wherein, $R^1$ is independently selected from H, $C_1$-$C_{10}$ linear or branched or cyclic alkyl, substituted or unsubstituted aryl, ester, ether, hetero aryl, halo, haloalkyl; 'z' is selected from C, N, S or O; and n=0 to 7 comprising the steps of:

(I) reacting ester compound (1^A) represented by the following formula,

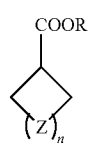

(1^A)

wherein, R is independently selected from H, $C_1$-$C_{10}$ linear or branched or cyclic alkyl, substituted or unsubstituted aryl, ester, ether, hetero aryl, halo, haloalkyl; 'z' is selected from C, N, S or O; and n=0 to 7.

with N-tert-butanesulfinylimine compound (2) represented by the following formula,

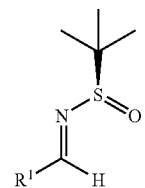

(2)

in the presence of base, to provide compound (3^A);

(II) reducing and cyclization of the compound (3^A) of stage (I) represented by the following formula,

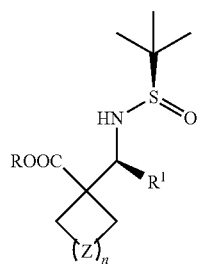

(3^A)

in the presence of a reducing agent, to provide compound (4^A);

(III) removing the sulfinyl group from the azaspiro intermediate compound (4^A) of stage (II) represented by the following formula,

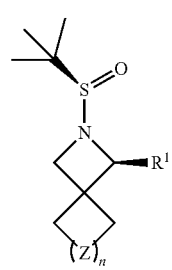

(4^A)

to provide compound (5^A).

The compound (5^A) obtained by the afore described process is optionally converted into various therapeutically active drugs or advanced drug intermediates.

The process of the present invention as per the specific embodiment described above is illustrated in the following Scheme (A);

Scheme (A)

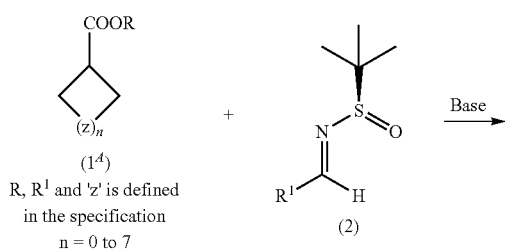

(1^A)

R, R¹ and 'z' is defined
in the specification
n = 0 to 7

+ 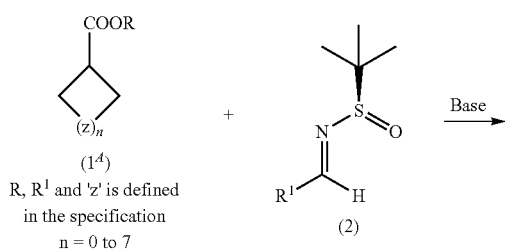 (2)

Base →

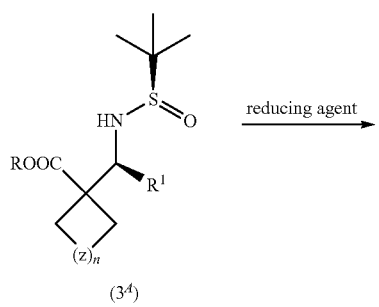

(3^A)

reducing agent →

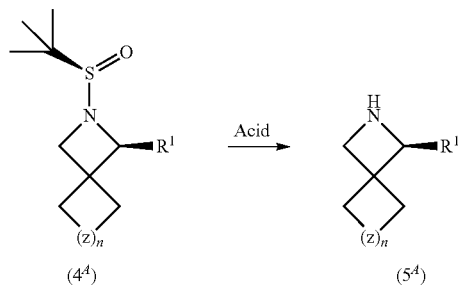

(4^A)  Acid →  (5^A)

In an embodiment, the base used is lithium base selected from Lithium bis(trimethylsilyl)amide (LiHMDS), Lithium diisopropylamide (LDA) or Lithium tetramethylpiperidide (LiTMP).

In an embodiment, the lithium base used is Lithium bis(trimethylsilyl)amide (LiHMDS).

In one aspect, there is provided a process for the preparation of azaspiro compound (5^A) in which 'z' is C and n=1 represented by the azaspiro compound (5) of the following formula,

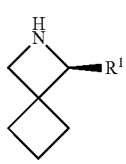

(5)

wherein, R¹ is independently selected from H, $C_1$-$C_{10}$ linear or branched or cyclic alkyl, substituted or unsubstituted aryl, ester, ether, hetero aryl, halo, haloalkyl.

Accordingly, the present invention relates to an improved process for the preparation of azaspiro compound (5) represented by the following formula,

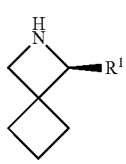

(5)

wherein, R¹ is independently selected from H, $C_1$-$C_{10}$ linear or branched or cyclic alkyl, substituted or unsubstituted aryl, ester, ether, hetero aryl, halo, haloalkyl;

comprising the steps of:

(a) reacting the ester compound (1) represented by the following formula,

(1)

wherein, R is independently selected from H, $C_1$-$C_{10}$ linear or branched or cyclic alkyl, substituted or unsubstituted aryl, ester, ether, hetero aryl, halo, haloalkyl.

with N-Cert-butanesulfinylimine compound (2) represented by the following formula,

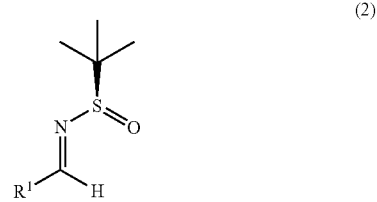

(2)

in the presence of lithium base, to provide compound (3);

(b) reducing and cyclization of the compound (3) of stage (a) represented by the following formula,

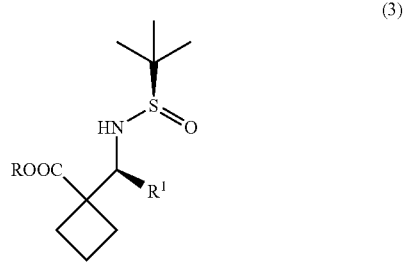

(3)

in the presence of a reducing agent, to provide compound (4);

(c) removing the sulfinyl group from the azaspiro intermediate compound (4) of stage (b) represented by the following formula,

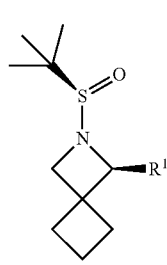

(4)

to provide compound (5).

The compound (5) obtained by the afore described process is optionally converted into various therapeutically active drugs or advanced drug intermediates.

The process of the present invention as per the specific embodiment described above is illustrated in the following Scheme (B);

Scheme (B)

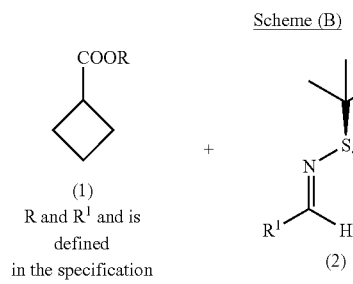

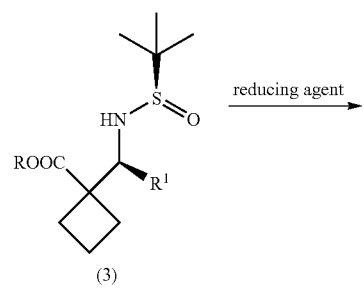

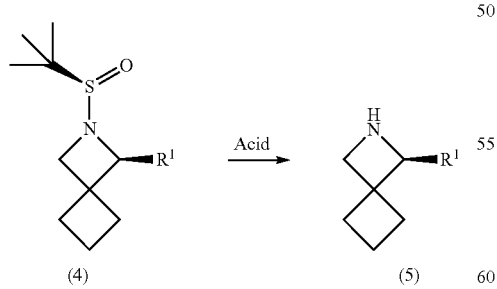

Accordingly, the present invention relates to an improved process for the preparation of azaspiro intermediate compound (4) represented by the following formula,

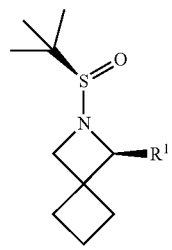

(4)

wherein, $R^1$ is independently selected from H, $C_1$-$C_{10}$ linear or branched or cyclic alkyl, substituted or unsubstituted aryl, ester, ether, hetero aryl, halo, haloalkyl;

comprising the steps of:

(x) reacting cyclobutane carboxylate ester compound (1') represented by the following formula,

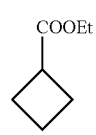

(1')

with N-tert-butanesulfinylimine compound (2) represented by the following formula,

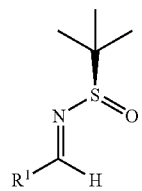

(2)

in the presence of Lithium bis(trimethylsilyl)amide (LiHMDS), (y) reducing and cyclization of the cyclobutane carboxylate ester intermediate compound (3') of stage (x) represented by the following formula,

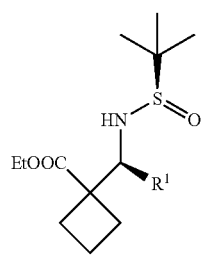

(3')

in the presence of a reducing agent.

The compound (4) obtained by the afore described process is optionally converted into azaspiro compound (5) by removing the sulfinyl group from the azaspiro intermediate compound (4).

In the context of the present invention, the term "optionally" when used in reference to any element; including a process step e.g. optionally converted; it is intended to mean that the subject compound is subsequently converted, or alternatively, is not converted into the compound (5). Both alternatives are intended to be within the scope of the present invention.

In an embodiment, the reducing agent is selected from metal hydride.

In an embodiment, the reducing agent is selected from Lithium aluminium hydride (LiAlH$_4$).

In a specific embodiment, the process for the preparation of azaspiro compound (5) comprises the steps of;
(i) dissolving carboxylate ester compound (1) in a solvent;
(ii) adding N-tert-butanesulfinylimine compound (2) to the stirring solution of stage (i);
(iii) cooling the reaction mixture of stage (ii) to a temperature of about −78° C.; (iv) adding Lithium bis(trimethylsilyl)amide (LiHMDS) to the stirring solution of stage (iii);
(v) optionally, isolating the compound (3) obtained from stage (iv);
(vi) treating the compound (3) of stage (v) with lithium aluminium hydride (LiAlH$_4$) in a solvent;
(vii) stirring the reaction mixture of stage (vi) at a temperature of about 0° C.;
(viii) adding sodium hydride (NaH) and p-toluenesulfonyl chloride (TsCl) to the solution of stage (vii);
(ix) removing the sulfinyl group.

The process of the present invention as per the specific embodiment described above is illustrated in the following Scheme (C);

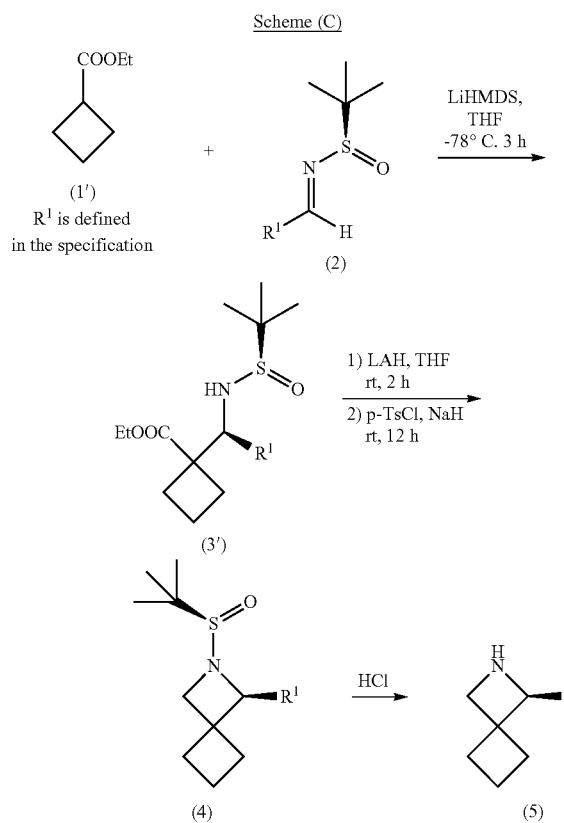

In the process, the solvent used in any of the process steps from the step (i) to step (ix) of the above process (as depicted in the Scheme (C)) is selected from an ether solvent such as tetrahydrofuran, cyclopentyl methyl ether, 2-methyltetrahydrofuran, diethyl ether, dioxane, 1,4-dioxane, 1,2-dioxane and 1,3-dioxane; an alcoholic solvent such as methanol, ethanol, isopropanol, t-amyl alcohol, t-butyl alcohol and hexanol; halogenated solvent such as dichloromethane, 4-bromotoluene, diiodomethane, carbon tetrachloride, chlorobenzene and chloroform; ketone such as acetone; an aprotic solvent such as acetonitrile, N,N-dimethyl formamide (DMF), N,N-dimethyl acetamide, dimethyl sulfoxide (DMSO) and N-methylpyrrolidone (NMP); an aromatic solvent such as toluene, xylene and benzene; water or a mixture thereof.

The term 'temperature of about −78° C.' referred to in the step (iii) of the above process (as depicted in the Scheme (A)) can range from −70° C. to −90° C.

The term 'temperature of about 0° C.' referred to in the step (vii) of the above process (as depicted in the Scheme (A)) can range from −5° C. to +5° C.

The term 'isolating' the compound referred to in any process step from step (i) to step (ix) corresponds to the isolating or separating the obtained product using methods that corresponds to the steps involving addition of water, biphasic solvent workup, separation of solvent layers or precipitation, evaporation of solvent, filtration, washing and drying.

The term 'removing the sulfinyl group' the compound referred to in any process step (ix) corresponds to the cleaving of the sulfinyl substitution of the amine and producing the free amine compound. The removal of the sulfinyl group is achieved by treatment of the compound (4) with an acid, for example Hydrochloric acid.

The inventors of the instant invention reasoned that a direct method to access enantiopure 1-substituted 2-azaspiro[3.3]heptane compounds would be an asymmetric synthesis comprising addition of a cyclobutane carboxylate anion to a Davis-Ellman's imine, followed by reduction and cyclisation, which has not been explicitly reported in the art on the currently considered chemical moieties. These reaction conditions, however, surprisingly led to an unusual substrate specific highly diastereoselective as well as enantioenriched 1-substituted 2-azaspiro[3.3]heptane compounds with diastereoselectively (dr values up to 98:2), and also with the improved yield of about 90%. The inventors of the instant invention also report that the process can be done as one pot procedure in order to save on cost. The inventors envisage that this synthetic effort could be of value in a variety of research applications, including the discovery of the known as well as new bioactive substances or chemical entities, many drugs, investigational drug candidates, and natural products and so on.

The process of the present invention as per the specific embodiment described above is illustrated in the following Scheme (D);

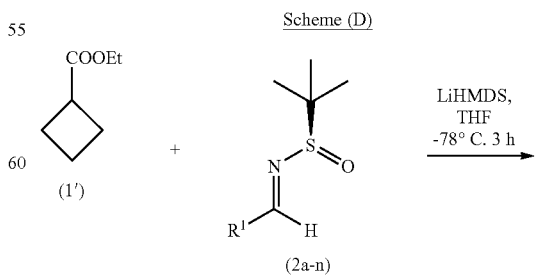

-continued

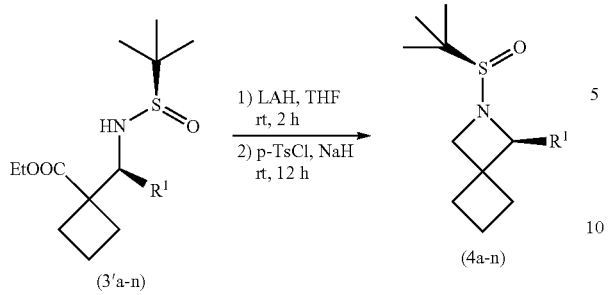

wherein R¹ represents variable as listed in below Table-1.

In the representative case illustrated below wherein the addition of ethyl cyclobutanecarboxylate ester compound (1') to various N-tert-butanesulfinylimines (2a-n) was studied. For instance, the reaction of 2a-n with ethyl cyclobutanecarboxylate ester compound (1') in the presence of LiHMDS in THF at −78° C. for 3 h, followed by reduction and cyclisation afforded corresponding 1-substituted 2-azaspiro[3.3]heptane compounds (4a-n) in about 90% yield and with a high diastereomeric ratio (dr of 98:2). The diastereoselectivity of the reaction was determined to be 98:2 by $^1$H NMR analysis. The obtained compound (4a-n) was further treated with hydrochloric acid to remove the sulfinyl group.

TABLE 1

Diastereoselective addition of ethyl cyclobutanecarboxylate ester compound (1') to various N-tert-Butanesulfinyl Aldimines

| Substrate (R¹) | product | yield (%)$^a$ | dr |
|---|---|---|---|
| 2a: R¹ = Ph | 4a | 89 | 98:2 |
| 2b: R¹ = p-MeC₆H₅ | 4b | 85 | 98:2 |
| 2c: R¹ = p-MeOC₆H₅ | 4c | 82 | 98:2 |
| 2d: R¹ = p-FC₆H₅ | 4d | 90 | 98:2 |
| 2e: R¹ = p-ClC₆H₅ | 4e | 86 | 98:2 |
| 2f: R¹ = p-CF₃C₆H₅ | 4f | 85 | 98:2 |
| 2g: R¹ = naphthalene | 4g | 90 | 98:2 |
| 2h: R¹ = anthracene | 4h | 81 | 98:2 |
| 2i: R¹ = phenanthrene | 4i | 82 | 98:2 |
| 2j: R¹ = 3-pyridyl | 4j | 74 | 98:2 |
| 2k: R¹ = 2-Furyl | 4k | 78 | 98:2 |
| 2l: R¹ = 2-Thiophenyl | 4l | 75 | 98:2 |
| 2m: R¹ = iso-butyl | 4m | 70 | 98:2 |
| 2n: R¹ = n-butyl | 4n | 72 | 98:2 |

$^a$All yields are of isolated product. Performed with ethyl cyclobutanecarboxylate 1' (3.0 equiv N-tert-butanesulfinyl aldimine 2 (1.0 equiv), LiHMDS (1.5 equiv) at −78° C. in THF for 3 h.

It is evident that, the instantly presented invention is an unusual substrate specific method for highly diastereoselective as well as enantioenriched 1-substituted 2-compounds with diastereoselectively (dr values up to 98:2), and also with the improved yield of about 90%. The compound (4) obtained by the afore described process is optionally converted into azaspiro compound (5) by removing the sulfinyl group from the azaspiro intermediate compound (4).

Additional, the structure and absolute stereochemistry of compound (4) was confirmed by single-crystal X-ray diffraction analysis. For instance, the structure and absolute stereochemistry of compound (Rs, R)-4l was confirmed by single-crystal X-ray diffraction analysis, as represented by FIG. 1).

In another aspect, there is provided a process for the preparation of the azaspiro compound ($5^A$) in which 'z' is N and n=1 represented by the diazaspiro compound ($5^N$) of the following formula,

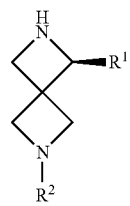

(5$^N$)

wherein, R¹ is independently selected from H, $C_1$-$C_{10}$ linear or branched or cyclic alkyl, substituted or unsubstituted aryl, ester, ether, hetero aryl, halo, haloalkyl; R² is independently selected from H, alkyl, aryl or N-protecting group.

In yet another aspect, the present invention relates to an improved process for the preparation of diazaspiro compound ($5^N$) represented by the following formula,

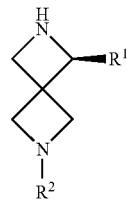

(5$^N$)

wherein, R¹ is independently selected from H, $C_1$-$C_{10}$ linear or branched or cyclic alkyl, substituted or unsubstituted aryl, ester, ether, hetero aryl, halo, haloalkyl; R² is independently selected from H, alkyl, aryl or N-protecting group; comprising the steps of:

(a¹) reacting the ester compound ($1^N$) represented by the following formula,

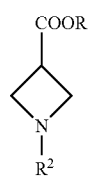

(1$^N$)

wherein, R is independently selected from H, $C_1$-$C_{10}$ linear or branched or cyclic alkyl, substituted or unsubstituted aryl, ester, ether, hetero aryl, halo, haloalkyl;
with N-tert-butanesulfinylimine compound (2) represented by the following formula,

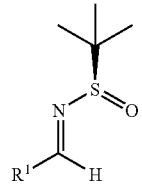

(2)

in the presence of lithium base, to provide compound ($3^N$);
(b¹) reducing and cyclization of the compound ($3^N$) of stage (a¹) represented by the following formula,

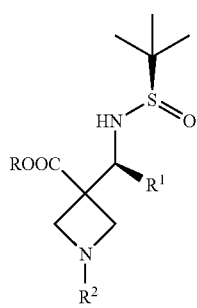

(3^N)

in the presence of a reducing agent, to provide compound (4^N);

(c') removing the sulfinyl group from the diazaspiro intermediate compound (4^N) of stage (b¹) represented by the following formula,

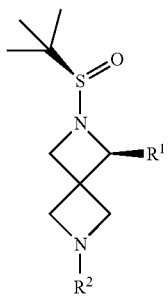

(4^N)

to provide compound (5^N).

The compound (5^N) obtained by the afore described process is optionally converted into various therapeutically active drugs or advanced drug intermediates.

The process of the present invention as per the specific embodiment described above is illustrated in the following Scheme (E);

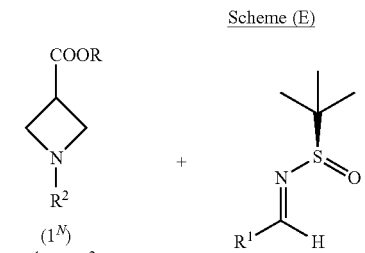

Scheme (E)

R, R¹ and R² is defined in the specification

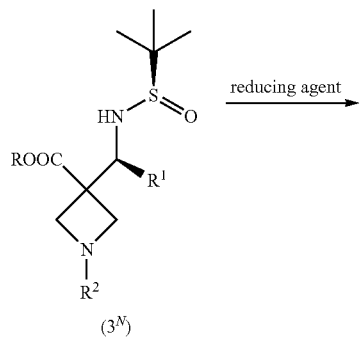

(3^N)

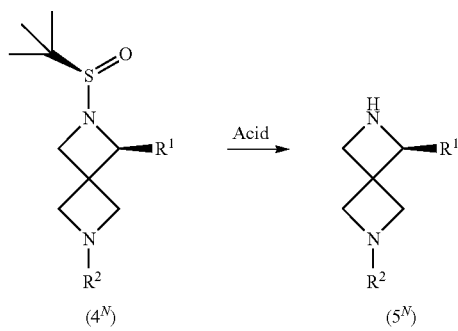

(4^N)                    (5^N)

Accordingly, the present invention relates to an improved process for the preparation of diazaspiro intermediate compound (4^N) represented by the following formula,

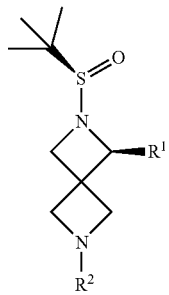

(4^N)

wherein, R¹ is independently selected from H, $C_1$-$C_{10}$ linear or branched or cyclic alkyl, substituted or unsubstituted aryl, ester, ether, hetero aryl, halo, haloalkyl; R² is independently selected from H, alkyl, aryl or N-protecting group;

comprising the steps of (x¹) reacting cyclobutane carboxylate ester compound (1^N') represented by the following formula,

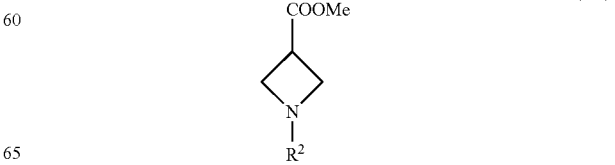

(1^N')

with N-tert-butanesulfinylimine compound (2) represented by the following formula,

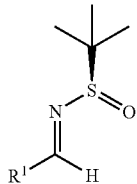

(2)

in the presence of Lithium bis(trimethylsilyl)amide (LiHMDS),
($y^1$) reducing and cyclization of the cyclobutane carboxylate ester intermediate compound ($3^N$) of stage ($x^1$) represented by the following formula,
in the presence of a reducing agent.

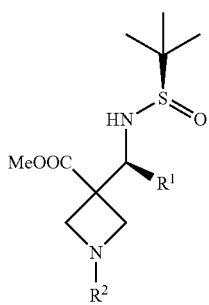

($3^{Ni}$)

The compound ($4^N$) obtained by the afore described process is optionally converted into diazaspiro compound ($5^N$) by removing the sulfinyl group from the diazaspiro intermediate compound ($4^N$).

The process of the present invention as per the specific embodiment described above is illustrated in the following Scheme (F);

Scheme (F)

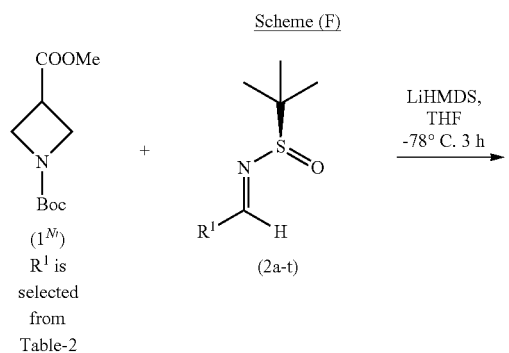

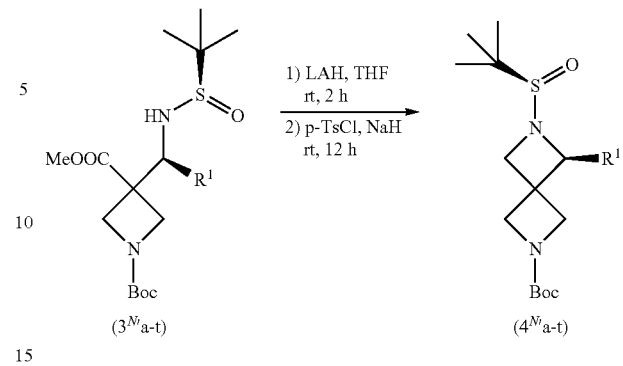

wherein $R^1$ represents variable as listed in below Table-2.

In the representative case illustrated below wherein the addition of methyl cyclobutanecarboxylate ester compound ($1N^1$) to various N-tert-butanesulfinylimines (2a-t) was studied. For instance, the reaction of 2a-t with methyl cyclobutanecarboxylate ester compound ($1^N$) in the presence of LiHMDS in THF at −78° C. for 3 h, followed by reduction and cyclisation afforded corresponding 1-substituted 2-diazaspiro[3.3]heptane compounds (4a-t) in about 90% yield and with a high diastereomeric ratio (dr 98:2). The diastereoselectivity of the reaction was determined to be 98:2 by $^1$H NMR analysis. The obtained compound (4a-t) was further treated with hydrochloric acid to remove the sulfinyl group.

TABLE 2

Diastereoselective addition of Methyl cyclobutanecarboxylate ester compound ($1^{Ni}$) to various N-tert-Butanesulfinyl aldimines:

| Substrate ($R^1$) | product | yield (%)$^a$ | dr |
|---|---|---|---|
| 2a: $R^1$ = Ph | $4^N$a | 85 | 98:2 |
| 2d: $R^1$ = p-FC$_6$H$_5$ | $4^N$d | 85 | 98:2 |
| 2f: $R^1$ = p-CF$_3$C$_6$H$_5$ | $4^N$f | 82 | 98:2 |
| 2g: $R^1$ = naphthalene | $4^N$g | 81 | 92:8 |
| 2i: $R^1$ = phenanthrene | $4^N$i | 78 | 98:2 |
| 2l: $R^1$ = 2-Thiophenyl | $4^N$l | 81 | 98:2 |
| 2m: $R^1$ = iso-butyl | $4^N$m | 78 | 98:2 |
| 2p: $R^1$ = p-F,o-Cl—C$_6$H$_3$ | $4^N$p | 80 | 90:10 |
| 2q: $R^1$ = 3-Furyl | $4^N$q | 85 | 98:2 |
| 2r: $R^1$ = tert-butyl | $4^N$r | 75 | 90:10 |
| 2s: $R^1$ = —C$_2$H$_4$—C$_6$H$_5$ | $4^N$s | 74 | 98:2 |
| 2t: $R^1$ = —C$_2$H$_2$—C$_6$H$_5$ | $4^N$t | 82 | 98:2 |

$^a$All yields are of isolated product. Performed with ethyl cyclobutanecarboxylate 1' (3.0 equiv N-tert-butanesulfinyl aldimine 2 (1.0 equiv), LiHMDS (1.5 equiv) at −78° C. in THF for 3 h.

Advantageously, the above identified elements of the process of the instant invention effectively contribute to the reduction of overall cost of the process.

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present invention.

EXAMPLES

Example-1: Ethyl1-((S)—(((R)-tert-butylsulfinyl) amino)(4chlorophenyl) methyl) cyclobutane-1-carboxylate (3'e)

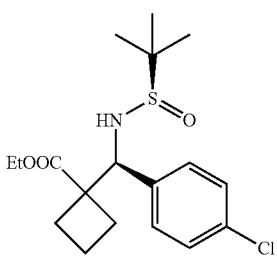 [SMILES: CCOC(=O)C1([C@@H](N[S@](=O)C(C)(C)C)c2ccc(Cl)cc2)CCC1]

Charged 5 V of anhydrous tetrahydrofuran (THF) in a flask followed by the addition of ethyl cyclobutanecarboxylate (1') (1.5 g, 12.34 mmol) and N-tert-butanesulfinylimines (2e) (1.00 g, 4.11 mmol). The reaction mixture was cooled down to a temperature of about −78° C. and to the stirring solution was added LiHMDS (1.0 M in THF, 10.20 mmol). The reaction mixture was cooled to a temperature of about −78° C. with continued stirring for about 3 h. The reaction mixture was quenched with water slowly and warmed to room temperature. The mixture was extracted with ethyl acetate (3×20 mL) and the combined organic extract was dried over sodium sulphate. The solvent was evaporated to provide the compound (3'e) with yield (1.44 g, 95%).

Example-2: (S)-2-((R)-tert-butylsulfinyl)-1-(4-chlorophenyl)-2-azaspiro[3.3]heptane (4e)

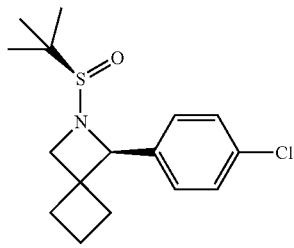 [SMILES: CC(C)(C)[S@@](=O)N1CC2(CCC2)[C@@H]1c1ccc(Cl)cc1]

Charged 10 V of anhydrous tetrahydrofuran (THF) in a flask followed by the addition of compound (Ye) (500 mg, 1.34 mmol) obtained as per procedure of example (1) and Lithium aluminium hydride (LiAlH$_4$) (1.0 M in THF, 2.0 mmol) at a temperature of about 0° C. The reaction mixture was stirred for 2 h under N$_2$ atmosphere at same temperature. The reaction mixture was quenched with saturated sodium sulfate (Na$_2$SO$_4$) solution (10 mL) and extracted with ethyl acetate (3×20 mL). The combined organic layer was evaporated to obtain the crude residue. To this crude residue was added anhydrous THF (2 mL) followed by the addition of sodium hydride (NaH) (4.0 mmol) and p-toluenesulfonyl chloride (TsCl) (1.5 mmol) at a temperature of about 0° C. The reaction mixture was further stirred for for 12 h at same temperature. The reaction mixture was quenched with water (10 mL) and extracted with ethyl acetate (3×20 mL). The combined organic layer was evaporated to provide the compound (4e) with yield (375 mg, 90.4%).

Example-3: (S)-1-(4-chlorophenyl)-2-azaspiro[3.3] heptane (5e)

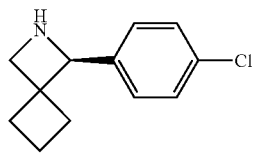 [SMILES: Clc1ccc([C@@H]2NCC23CCC3)cc1]

Charged 3V of 1,4-dioxane in a flask followed by the addition of compound 4e (500 mg, 1.4 mmol) obtained as per procedure of example (2) and hydrochloric acid solution (4.0 M in dioxane, 10V). The reaction mixture was stirred for 2 h at room temperature and the reaction mixture was concentrated under vacuum. To the crude residue was added water, followed by the addition of 6 M NaOH aqueous solution to adjust the pH 12-13. The reaction mixture was extracted with ethyl acetate (5V) and the separated organic layer was evaporated to provide the azaspiro compound (5e) with yield (350 mg, 98%).

Example-4: Ethyl 1-((R)—(((R)-tert-butylsulfinyl) amino)(thiophen-2-yl)methyl)cyclobutane-1-carboxylate (3'l)

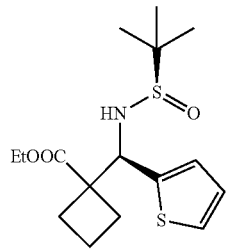 [SMILES: CCOC(=O)C1([C@@H](N[S@](=O)C(C)(C)C)c2cccs2)CCC1]

Charged 5 V of anhydrous tetrahydrofuran (THF) in a flask followed by the addition of ethyl cyclobutanecarboxylate (1') (1.7 g, 13.9 mmol) and N-tert-butanesulfinylimines (2l) (1.00 g, 4.65 mmol). The reaction mixture was cooled down to a temperature of about −78° C. and to the stirring solution was added LiHMDS (1.0 M in THF, 11.6 mmol). The reaction mixture continued stirring for about 3 h at a the temperature of about −78° C. The reaction mixture was quenched with water slowly and warmed to room temperature. The mixture was extracted with ethyl acetate (3×20 mL) and the combined organic extract was dried over sodium sulphate. The solvent was evaporated to provide the compound (3'l) with yield (1.4 g, 88%).

Example-5: (R)-2-((R)-tert-butylsulfinyl)-1-(thiophen-2-yl)-2azaspiro[3.3]heptane (4l)

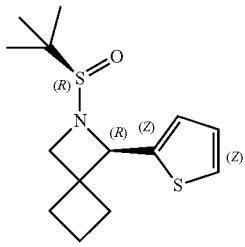

Charged 10 V of anhydrous tetrahydrofuran (THF) in a flask followed by the addition of compound (3'l) (500 mg, 1.45 mmol) obtained as per procedure of example (1) and Lithium aluminium hydride (LiAlH$_4$) (1.0 M in THF, 2.0 mmol) at a temperature of about 0° C. The reaction mixture was stirred for 2 h under N$_2$ atmosphere at same temperature. The reaction mixture was quenched with saturated sodium sulfate (Na$_2$SO$_4$) solution (10 mL) and extracted with ethyl acetate (3×20 mL). The combined organic layer was evaporated to obtain the crude residue. To this crude residue was added anhydrous THF (2 mL) followed by the addition of sodium hydride (NaH) (4.0 mmol) and p-toluenesulfonyl chloride (TsCl) (1.5 mmol) at a temperature of about 0° C. The reaction mixture was further stirred for for 12 h at same temperature. The reaction mixture was quenched with water (10 mL) and extracted with ethyl acetate (3×20 mL). The combined organic layer was evaporated to provide the compound (4l) with yield (348 mg, 85%). The structure and absolute stereochemistry of the compound (Rs, R)-4l was confirmed by single-crystal X-ray diffraction analysis (FIG. 1)).

Example-6: Methyl-1-benzhydryl-3-((S)—(((R)-tert-butylsulfinyl) amino)(phenyl) methyl) azetidine-3-carboxylate (3$^{N''}$a)

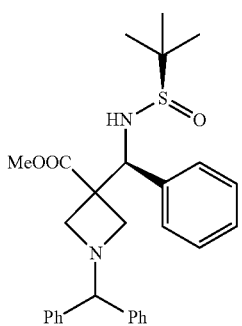 [SMILES: COC(=O)C1([C@@H](N[S@](=O)C(C)(C)C)c2ccccc2)CN(C(c2ccccc2)c2ccccc2)C1]

Charged 5 V of anhydrous tetrahydrofuran (THF) in a flask followed by the addition of methyl cyclobutanecarboxylate (1N'') (1.65 g, 6 mmol) and N-tert-butanesulfinylimines (2a) (0.41 g, 2 mmol). The reaction mixture was cooled down to a temperature of about −78° C. and to the stirring solution was added LiHMDS (1.0 M in THF, 5 mmol). The reaction mixture was cooled to a temperature of about −78° C. with continued stirring for about 3 h. The reaction mixture was quenched with water slowly and warmed to room temperature. The mixture was extracted with ethyl acetate (3×20 mL) and the combined organic extract was dried over sodium sulphate. The solvent was evaporated to provide the compound (3$^{N''}$a) with yield (0.91 g, 94%).

Example-7: (S)-6-benzhydryl-2-((R)-tert-butylsulfinyl)-1-phenyl-2,6-diazaspiro [3.3]heptane (4$^{N''}$a)

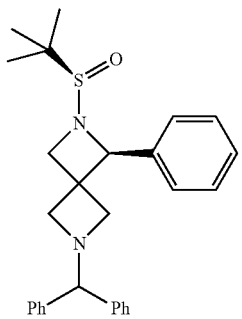 [SMILES: CC(C)(C)[S@@](=O)N1CC2(CN(C(c3ccccc3)c3ccccc3)C2)[C@@H]1c1ccccc1]

Charged 10 V of anhydrous tetrahydrofuran (THF) in a flask followed by the addition of compound (3$^{N''}$a) (500 mg, 1.02 mmol) obtained as per procedure of example-6 and Lithium aluminium hydride (LiAlH$_4$) (1.0 M in THF, 2.0 mmol) at a temperature of about 0° C. The reaction mixture was stirred for 2 h under N$_2$ atmosphere at same temperature. The reaction mixture was quenched with saturated sodium sulfate (Na$_2$SO$_4$) solution (10 mL) and extracted with ethyl acetate (3×20 mL). The combined organic layer was evaporated to obtain the crude residue. To this crude residue was added anhydrous THF (2 mL) followed by the addition of sodium hydride (NaH) (5.0 mmol) and p-toluenesulfonyl chloride (TsCl) (1.5 mmol) at a temperature of about 0° C. The reaction mixture was further stirred for for 12 h at same temperature. The reaction mixture was quenched with water (10 mL) and extracted with ethyl acetate (3×20 mL). The combined organic layer was evaporated to provide the compound (4$^{N''}$a) with yield (415 mg, 91%).

Example-8: (S)-6-benzhydryl-1-phenyl-2,6-diazaspiro[3.3]heptane (5$^{N''}$a)

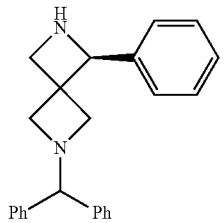 [SMILES: c1ccc(C(c2ccccc2)N2CC3(CN[C@H]3c3ccccc3)C2)cc1]

Charged 3V of 1,4-dioxane in a flask followed by the addition of compound 4$^{N''}$a (300 mg, 0.6747 mmol) obtained as per procedure of example (7) and hydrochloric acid solution (4.0 M in dioxane, 10V). The reaction mixture was stirred for 2 h at room temperature and the reaction mixture was concentrated under vacuum. To the crude residue was added water, followed by the addition of 6 M NaOH aqueous solution to adjust the pH 12-13. The reaction mixture was extracted with ethyl acetate (5V) and the separated organic layer was evaporated to provide the azaspiro compound ($5^Na$) with yield (220 mg, 95%).

We claim:

1. A process for the preparation of azaspiro or diazaspiro compound ($5^A$) of the following formula,

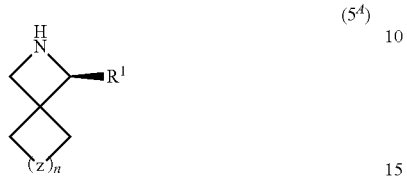

wherein, $R^1$ is independently selected from H, $C_1$-$C_{10}$ linear or branched or cyclic alkyl, substituted or unsubstituted aryl, ester, ether, heteroaryl, halo, or haloalkyl; 'z' is selected from C, N, S or O; and n=0 to 7 comprising the steps of:
(a) reacting ester compound ($1^A$) represented by the following formula,

wherein, R is independently selected from H, $C_1$-$C_{10}$ linear or branched or cyclic alkyl, substituted or unsubstituted aryl, ester, ether, heteroaryl, halo, or haloalkyl; 'z' is selected from C, N, S or O; and n=0 to 7,
with sulfinylimine compound (2') represented by the following formula,

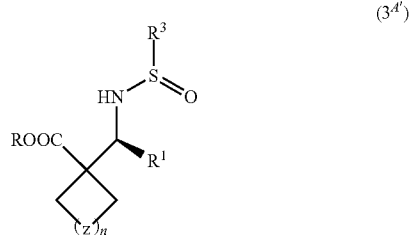

wherein, $R^3$ is independently selected from t-butyl or p-tolyl;
in the presence of base, to provide compound ($3^{A'}$);
(b) reducing and cyclization of the compound ($3^{A'}$) of stage (a) of the following formula,

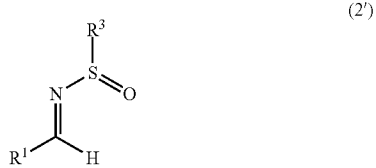

in the presence of a reducing agent, to provide compound ($4^{A'}$);
(c) removing the sulfinyl group from the azaspiro or diazaspiro intermediate compound ($4^{A'}$) of stage-(b) of the following formula,

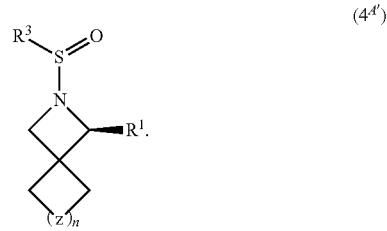

2. The process according to claim 1, wherein the base used in step (a) is lithium base selected from Lithium bis(trimethylsilyl)amide (LiHMDS), Lithium diisopropylamide (LDA) or Lithium tetramethylpiperidide (LiTMP).

3. The process according to claim 1, wherein the reducing agent used in step (b) is a metal hydride selected from Lithium aluminium hydride ($LiAlH_4$).

4. The process according to claim 1, wherein the removing the sulfinyl group in step (c) is achieved by treatment with an acid selected from hydrochloric acid.

5. The process according to claim 1, wherein the azaspiro compound ($5^A$) in which 'z' is C and n=1 represented by the azaspiro compound (5) of the following formula,

wherein, $R^1$ is independently selected from H, $C_1$-$C^{10}$ linear or branched or cyclic alkyl, substituted or unsubstituted aryl, ester, ether, heteroaryl, halo, or haloalkyl;

is prepared by the process comprising the steps of:
(x) reacting the cyclobutane carboxylate ester compound (I') of the following formula,

with N-tert-butanesulfinylimine compound (2) of the following formula,

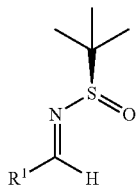

(2)

in the presence of Lithium bis(trimethylsilyl)amide (LiHMDS), to provide compound (3');
(y) reducing and cyclization of the cyclobutane carboxylate ester intermediate compound (3) of stage (x) of the following formula,

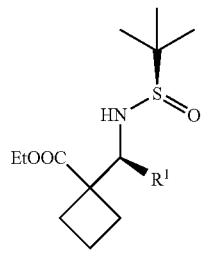

(3')

in the presence of Lithium aluminium hydride ($LiAlH_4$) to yield compound (4);
(z) removing the sulfinyl group from the azaspiro intermediate compound (4) of stage (y) represented by the following formula,

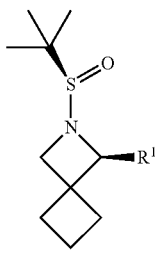

(4)

in the presence of hydrochloric acid to provide compound (5).

6. The process according to claim 1, wherein the azaspiro compound ($5^A$) in which 'z' is N and n=1 represented by the diazaspiro compound ($5^N$) of the following formula,

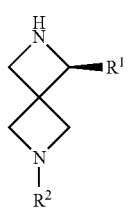

($5^N$)

wherein, $R^1$ is independently selected from H, $C_1$-$C_{10}$ linear or branched or cyclic alkyl, substituted or unsubstituted aryl, ester, ether, heteroaryl, halo, or haloalkyl; $R^2$ is independently selected from H, alkyl, aryl or N-protecting group;

is prepared by the process comprising the steps of:
($a^1$) reacting the ester compound ($1^N$) of the following formula,

($1^N$)

wherein, R is independently selected from H, $C_1$-$C_{10}$ linear or branched or cyclic alkyl, substituted or unsubstituted aryl, ester, ether, heteroaryl, halo, or haloalkyl,
with N-tert-butanesulfinylimine compound (2) represented by the following formula,

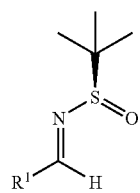

(2)

in the presence of lithium base, to provide compound ($3^N$);
($b^1$) reducing and cyclization of the compound ($3^N$) of stage ($a^1$) of the following formula,

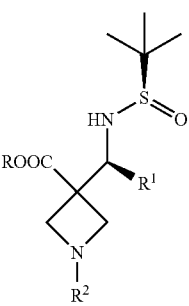

($3^N$)

in the presence of a reducing agent, to provide compound ($4^N$);
($c^1$) removing the sulfinyl group from the diazaspiro intermediate compound ($4^N$) of stage ($b^1$) represented by the following formula,

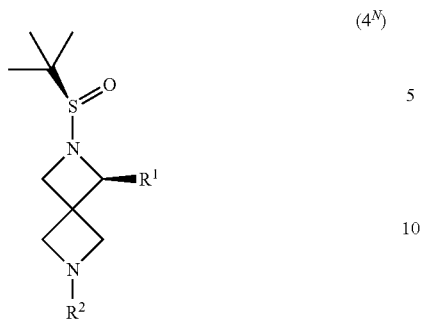

(4<sup>N</sup>)

to yield compound (5<sup>N</sup>).

7. The process according to claim 6, wherein the lithium base used in step (a¹) is selected from Lithium bis(trimethylsilyl)amide (LiHMDS), Lithium diisopropylamide (LDA) or Lithium tetramethylpiperidide (LiTMP).

8. The process according to claim 6, wherein the reducing agent used in step (b¹) is a metal hydride selected from Lithium aluminium hydride (LiAlH₄).

9. The process according to claim 6, wherein the removing the sulfinyl group in step (c¹) is achieved by treatment with an acid selected from hydrochloric acid.

* * * * *